United States Patent [19]
Weinberger

[11] Patent Number: 5,408,443
[45] Date of Patent: Apr. 18, 1995

[54] PROGRAMMABLE MEDICATION DISPENSING SYSTEM

[75] Inventor: Edward D. Weinberger, New York, N.Y.

[73] Assignee: Polypharm Corp., New York, N.Y.

[21] Appl. No.: 92,352

[22] Filed: Jul. 15, 1993

Related U.S. Application Data

[63] Continuation-in-part of Ser. No. 932,072, Aug. 19, 1992, abandoned.

[51] Int. Cl.⁶ ............... G04B 47/00; A47B 67/02; G08B 1/00
[52] U.S. Cl. ............................. 368/10; 221/3; 340/309.15
[58] Field of Search ............ 368/10, 107–109; 221/2, 3, 15; 340/309.15, 309.4; 364/413.02, 569

[56] References Cited

U.S. PATENT DOCUMENTS

| | | |
|---|---|---|
| 3,871,551 | 3/1975 | Bender . |
| 4,223,801 | 9/1980 | Carlson . |
| 4,361,408 | 11/1982 | Wirtschafter . |
| 4,504,153 | 3/1985 | Schollmeyer et al. . |
| 4,588,303 | 5/1986 | Wirtschafter et al. . |
| 4,611,924 | 9/1986 | Stasin . |
| 4,660,991 | 4/1987 | Simon . |
| 4,695,954 | 9/1987 | Rose et al. . |
| 4,717,042 | 1/1988 | McLaughlin ............ 221/3 |
| 4,725,997 | 2/1988 | Urquhart et al. . |
| 4,731,765 | 3/1988 | Cole et al. . |
| 4,748,600 | 5/1988 | Urquhart . |
| 4,768,176 | 8/1988 | Kehr et al. . |
| 4,768,177 | 8/1988 | Kehr et al. . |
| 4,858,207 | 8/1989 | Buchner . |
| 4,911,327 | 3/1990 | Shepherd et al. . |
| 4,939,705 | 7/1990 | Hamilton et al. . |
| 4,962,491 | 10/1990 | Schaffer ............ 368/21 |
| 4,970,669 | 11/1990 | McIntosh et al. . |
| 5,020,037 | 5/1991 | Raven . |
| 5,088,056 | 2/1992 | McIntosh et al. . |
| 5,099,463 | 8/1992 | Lloyd et al. . |
| 5,170,380 | 12/1992 | Howard et al. ............ 368/10 |
| 5,200,891 | 4/1993 | Kehr et al. ............ 368/10 |
| 5,289,157 | 2/1994 | Buokk et al. ............ 340/309.15 |

FOREIGN PATENT DOCUMENTS

2650420 2/1991 France .

*Primary Examiner*—Vit W. Miska
*Attorney, Agent, or Firm*—Brumbaugh, Graves, Donohue & Raymond

[57] ABSTRACT

A medication-dispensing system includes a prescribing data entry station for use by a physician to store prescription information in a portable prescribing module, a dispensing data entry station for use by a pharmacist to store dispensing information in a portable dispensing data storage unit, and a medication dispenser responsive to information stored in the portable prescribing module to describe use of medication in the dispenser in accordance with a regimen prescribed by the physician and to the dispensing data storage unit to control dispensing of the medication. One embodiment has two medication drawers, each having a plurality of compartments with indicating lights selectively indicating the compartment from which medication is to be taken, a screen for displaying instructions regarding loading of the medication compartments and taking of the medication, and a keyboard including a confirming entry key for actuation by the user to confirm compliance with the instructions. Another embodiment has a series of medication-containing compartments, each covered by a separate sliding or folding cover.

31 Claims, 3 Drawing Sheets

PROGRAMMABLE MEDICATION DISPENSING SYSTEM

REFERENCE TO RELATED APPLICATION

This application is a continuation-in-part of the application of Edward D. Weinberger, Ser. No. 07/932,072 filed Aug. 19, 1992, now abandoned.

BACKGROUND OF THE INVENTION

This invention relates to medicine-dispensing devices and, more particularly, to a programmable medicine-dispensing system.

Heretofore, a variety of medicine-dispensing devices have been proposed. In the patent to Rose et al., U.S. Pat. No. 4,695,954, for example, a medication-dispensing system is provided in which prescription information is encoded into a memory card by a programming device located at a pharmacy in accordance with a physician's instructions. The memory card is inserted by the patient into a dispenser which automatically releases the appropriate medication at the required times and provides a corresponding alarm and visual indication on a screen. The dispenser includes sensors which detect the removal of medication from a delivery compartment to record compliance by the patient, but failure of the patient to remove the medication will not prevent the dispenser from continuing its programmed operation but instead may send an alarm to a remote location. This system is intended for use by a patient at a facility where supervising personnel can observe monitors and take corrective action promptly, but is not portable or useful in an environment where the patient must follow a regimen without close supervision by others.

The patent to Urquhart et al. U.S. Pat. No. 4,725,997 discloses a dispensing device for pharmaceutical preparations which is programmed with information concerning a dosing regimen and permits the user to deviate within limits from the regimen and monitors the deviations while preventing dispensing outside the predetermined limits. The dispensing device has a data communication interface for communicating with a physician or pharmacist and includes a display screen on which instructions and inquiries may be displayed.

The Mcintosh et al. U.S. Pat. No. 4,088,056 discloses a programmed medication clock having a plurality of separate compartments for different types of medication along with a separate indicator and acknowledgment switch adjacent to each compartment to indicate the compartment from which medication is to be taken and to acknowledge taking of the medication by the user. The Lloyd et al. U.S. Pat. No. 5,099,463 shows a medication alarm device with separate holders for removable medication containers and corresponding indicator lights to designate a container from which medication is to be taken.

In the Schollmeyer et al. U.S. Pat. No. 4,504,153, a cap for a medication container includes a programmable prompting device which is programmed in accordance with the physician's prescription instructions to automatically prompt a patient to take medication at prescribed times. The prompting device is programmed by plugging it into a pharmacist's programming station which is connected to a computer for supplying programming instructions in accordance with the physician's prescription.

The Bender U.S. Pat. No. 3,871,551 discloses a pill dispenser usable by a patient with no supervision. According to that patent, a manually-advanced pill dispenser is provided for periodic delivery of medication at timed intervals and failure to remove a pill from the dispenser at the required time will prevent further advance of the dispensing system. The patents to Carlson, U.S. Pat. No. 4,223,801; Wirtschafter et al., U.S. Pat. No. 4,588,303; McLaughlin, U.S. Pat. No. 4,717,042; Cole et al., U.S. Pat. No. 4,731,765; and Shepherd et al., U.S. Pat. No. 4,911,327, similarly disclose dispensing arrangements in which removal of medication at the appropriate time is detected.

The Shepherd et al. patent also discloses a refill alarm, as does the Kehr et al. U.S. Pat. No. 4,768,176, and the latter patent also discloses an arrangement for dispensing prescribed drugs at variable times in accordance with the patient's activities. None of the prior art, however, provides a programmable medicine dispenser in which a separable data storage unit may be programmed by a physician or a pharmacist to provide specific instructions with respect to each drug to be taken and which also requires the patient to properly confirm that he has followed the instructions or which releases a drawer containing medications and provides a visual indication of the location of medication to be taken.

SUMMARY OF THE INVENTION

Accordingly, it is an object of the present invention to provide a programmable medicine-dispensing system which overcomes the above-mentioned disadvantages of the prior art.

Another object of the invention is to provide a programmable medicine-dispensing system which is appropriate for a patient who is not under immediate supervision.

These and other objects of the invention are attained by providing a programmable medicine-dispensing system including a removable data storage unit in which regimen-related information may be stored to make the information and appropriate medication available at required times and wherein the patient must make a confirming entry to permit the medication schedule to continue in accordance with the regimen. The regimen-related information may be entered in a prescribing information storage unit by a physician or in a dispensing information storage unit by a pharmacist or a physician or the patient, or it may be entered in the dispenser by the patient. In addition, the location of medication to be taken in a drawer containing several compartments may be designated by an illuminated indicator. Preferably, the system includes an arrangement for recording each confirming entry made by the user as well as any user information such as side effect indications.

The programmable medication-dispensing system of the invention is addressed to the management of multi-prescription regimens of "self-administering" or "home-care" patients with a minimum level of patient competency, for patients who might have a variety of attendants at different times, are under the care of more than one physician, and might obtain medication from different pharmacists. In its most comprehensive form, the system includes not only the dispenser used by the patient, but also the prescription card encoded by a pharmacist, a card encoder for the pharmacist, software for the pharmacist and for the physician and the user, and various accessories for communication and ancillary devices to facilitate the operation.

Although the dispenser can be embodied in many configurations, they all have certain basic design aspects and the same method of operation. In particular, the dispenser is a stand-alone unit which is portable, programmable, interactive with the patient, simple to use, has large-scale ergonomics and includes a memory and an alarm system, which may include both sound and voice signals, a TV-interrupt and a remote alarm. It may also be designed for telephonic communication, for example, with a physician or pharmacist.

Among the capabilities and features of the dispenser are the storage and display of information relating to interactions for all drugs to be taken by the patient, and the display of appropriate warnings for interactions which might be adverse, and a record of any patient toxicity, i.e., adverse drug reaction. The dispenser, which is programmable by either a PC or a "Smart Card" or similar module, can devise the optimal daily schedule for taking medication and can use a variety of loading strategies, either daily or cyclical, from bulk supplies or prepackaged or from bottled inventories.

At the actual time of dispensing the medication, the dispenser identifies the medication to be taken, specifies the quantity to be taken and provides instructions with respect to the taking of medication. Also, at predetermined intervals, the dispenser can query the patient as to any present symptomatic state and any drug response. Moreover, the dispenser requires active, positive "confirmation" from the patient that the medication was taken or specific instructions were read and followed, or that a response to a specific inquiry has been made. Furthermore, the system records the actual time and date when each medication was taken or any failure to take medication when scheduled and each confirmed event relating to the medication and any event for which confirmation by the patient is required.

With respect to the scheduled taking of medication, the schedule is based on prescribed interval tolerances and the dispenser may provide a variety of alarms, for example, of variable frequency and tone. It also displays the next scheduled taking, provides anticipatory alarms for "critical-to-take" medications and, if any medication is taken early or delayed, it can reschedule all of the remaining drugs to be taken during that day. The dispenser further distinguishes between a "postponed" taking of medication and a "late" taking of medication, and has an iterative procedure for scheduled but "moving" events and can also adjust dosages.

With respect to unscheduled ("as-needed") taking of medication, the system can display the limits on cumulative daily dose and frequency and can condition dispensing on responses to specific inquiries, such as prior symptomatic states.

The system can also intervene at any time by, for example, alerting the patient with respect to a "critical" failure to take medication or toxicity, i.e., adverse drug reaction situations and can provide instructions to the patient regarding stoppage of medication and calling for aid. The system can also allow the patient to select any one of several applicable drugs. In addition, the system can be arranged to adjust dosages depending on the response of the patient to symptomatic inquiries and can recall and display stored information such as the last drug taken and the last time any drug was taken, for example, and can also provide more elaborated instructions if the patient is unable to understand abbreviated instructions provided periodically.

Furthermore, the medication-dispensing system may provide information about dressings, patient temperature, blood pressure, appointments and the like, and the patient can enter information regarding his condition or situation, i.e., the times of sleep, of mobility, of eating, of bodily functions and the like. The patient's dispenser may also be arranged to receive telephonic transmission of data and instructions, and a remote alarm and locator for the dispenser can also be provided. The dispenser can also maintain an inventory of pills within the dispenser and in the patient's bottled supply and can provide alarm signals alerting the user to reload, refill or reorder medication.

The system is especially adapted for the regulation of prescribed pharmaceuticals in which the timing, sequence and dosage of medication needs to be continuously adjusted or where the complexity of such management is greatly compounded by the prescription of more than one drug and where there is a wide range of patient competency for self-administration such as may occur in connection with patients over the age of sixty who require multiple medications for chronic conditions. Although the medication-dispensing system of the present invention has direct applicability to any regimen that requires a responsive and flexible drug strategy and a high confidence of patient compliance, it is particularly addressed to the prescription, coordination, interaction, instruction and periodic monitoring and special compliance problems relating to complex mono- and poly-pharmaceutical regimens.

In accordance with a preferred embodiment, the medication-dispensing system of the invention includes a prescribing data entry station at which instructions are encoded by a physician into a portable prescribing module. The prescribing module may, for example, be a microcomputer cartridge containing an appropriate memory in which instructions are stored and from which a physician may retrieve compliance information indicating the extent to which the patient has complied with instructions. Preferably, the prescribing module is encoded by using a personal computer attached to a prescribing adapter into which the prescribing module is plugged.

Preferably, the system also includes a dispensing data entry station at which a dispensing data storage module is programmed by a pharmacist, for example, to store drug-specific information relating to the medication, including times and dosages and refill information.

In addition, the system includes a medication dispenser operable by the patient in which the prescribing data storage module and the dispensing data storage module are received and which is responsive to the stored data to display appropriate medication information and permit loading and dispensing by the patient of the specific drugs prescribed by the physician. To assure compliance with the prescribing and dispensing instructions, the dispenser requires confirming entries to be made by the patient at each step in the process. If desired, the dispenser may have, for example, separate drawers for drugs to be taken on demand and drugs to be taken only at specified intervals, each drawer containing a series of compartments for different drugs with indicating lights designating the compartment containing the drug to be taken or loaded by the patient.

BRIEF DESCRIPTION OF THE DRAWINGS

Further objects and advantages of the invention will be apparent from a reading of the following description in conjunction with the accompanying drawings, in which.

DESCRIPTION OF PREFERRED EMBODIMENTS

Figure 1:
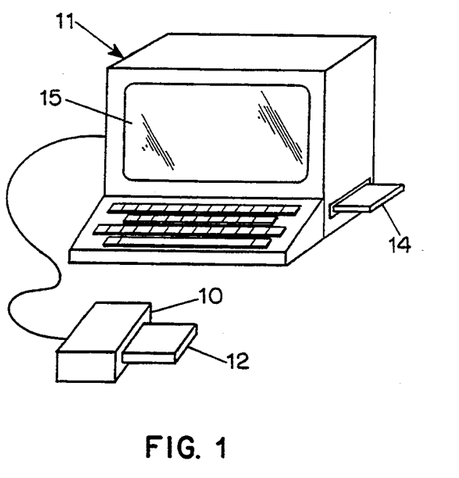
FIG. 1 is a schematic perspective view illustrating the arrangement of a representative prescribing data entry station for use by a physician in accordance with the invention.

In the typical programmable medication-dispensing system in accordance with the invention shown in FIGS. 1-4, a prescribing data entry station, shown in FIG. 1, includes a prescribing adapter 10, connected to a conventional personal computer 11 or the like, which is arranged to encode data and prescribing instructions, typically under the control of a physician, in a prescribing module 12 regarding the specific regimen, including the timing and dose of each of a plurality of drugs to be taken by a patient. The prescribing module may, for example, be a microcomputer cartridge of the usual type. The patient then uses the prescribing module to control the operation of a medication dispenser such as described hereinafter with reference to FIG. 3.

Referring more specifically to the illustration in FIG. 1, the computer 11 receives data from a series of diskettes 14 containing basic instructions and other information and displays the data as selected by the physician on a screen 15 to assist the physician in determining the drug regimen. In addition to a diskette containing basic instructions, other diskettes may include the medication history and most current prescribing instructions and schedule for the patient, specific information relating to each of the medications to be prescribed, including recommended dosages, interactions, counterindications, and the like, and condition- or disease-specific information, including a checklist or menu of choices that allows the physician to select dosage and time variables, to screen for specific drug interactions, to delineate particular symptoms, conditions, responses, instructions and the like, which are appropriate to the drugs prescribed, the patient competency level and the diagnosis. Such diskettes may be prepared, for example, under the guidance of a "physician (scientific) advisory committee" whose members include disease- or condition-specific doctors, gerontologists and polypharmacists.

Instead of diskettes, the same type of information may be supplied in the form of magnetic cards or other electronic or magnetic storage devices having a capacity sufficient to store all of the required information. Electronic storage devices may be in the form of "smart cards" containing embedded integrated circuits. Similarly, the prescribing module 12 and the dispensing module 18 described hereinafter may consist of any type of information storage device, such as a magnetic card or disk or an electronic storage device, which may be received in and read by an information-handling system.

After the prescribing module 12 has been plugged in and the data from the appropriate diskettes has been entered, the computer displays the necessary information on a screen 15, such as the competency level of the patient, and, for each drug prescribed, a menu is displayed from which the physician keys in the dosage and timing selections, limits and special instructions. A disease-specific menu is then displayed and the computer then conducts a drug interaction and counterindication review and displays any possible incompatibilities. Based on this information, the physician enters any changes to the initially-established regimen and selects the appropriate features or operating mode from the level of simplicity menu derived from the patient information file. Thereafter, the selected regimen and its schedules, which have been checked by the computer or the encoder for consistency, redundancy and efficiency, are displayed on the screen 15. When the physician has determined that the regimen is appropriate, the prescribing module 12 is encoded and the patient's information diskette is updated. The encoded prescribing module 12 can then be used by the patient to control the operation of the dispenser 13.

Figure 2:
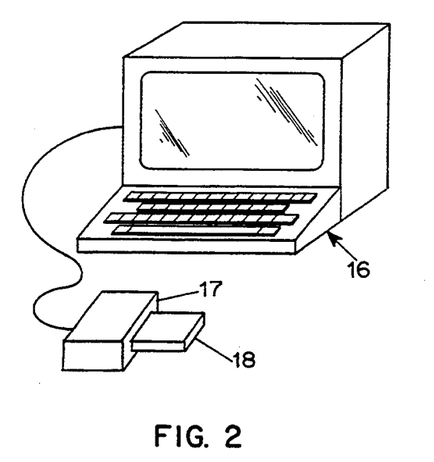
FIG. 2 is a schematic perspective view illustrating the arrangement of a typical dispensing data entry station for use by a pharmacist.

In order to obtain the medication to be dispensed by the dispenser, the patient provides a pharmacist with a written prescription from the physician. At the pharmacy, the pharmacist uses a dispensing data entry station, such as shown in FIG. 2, including a computer 16 with a dispensing module adapter 17 to encode a dispensing data storage module 18 with dispensing instructions. The dispensing module 18, which may also be in the form of a smart card or the like, is a one-time use item which is supplied to the patient with a specific quantity of medication. After that quantity has been used, the patient must have the original module or card reprogrammed or obtain another dispensing module or card, along with the appropriate quantity of the medication, from the pharmacist.

If desired, the pharmacist dispensing data entry station can be made with the computer 16 and the adapter 17 combined in a single box with a display screen.

Figure 3:
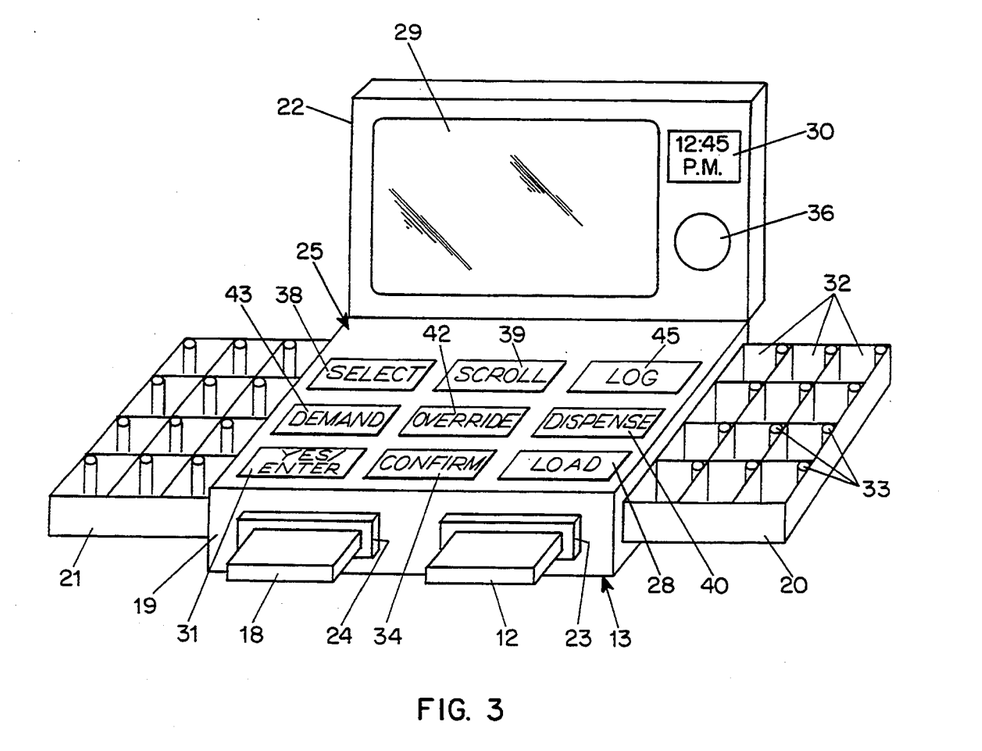
FIG. 3 is a schematic perspective view illustrating the arrangement of a representative medication dispenser arranged in accordance with the invention.

The typical embodiment of a programmable medicine dispenser 13 according to the invention, illustrated in FIG. 3, includes a rectangular box-like housing 19 having two drawers 20 and 21 slidably received in the sides of the housing and a hinged cover 22 containing a screen 29 which is adapted to be folded down on the top of the housing. One receptacle 23 at the bottom of the front of the housing is arranged to receive the prescribing module 12 which has been encoded by the physician's computer 11 in the manner described above with respect to FIG. 1 and another receptacle 24 receives the dispensing module 18 encoded by the pharmacist, as described in connection with FIG. 2. A keyboard 25 is provided on the top of the housing 13 to enter information necessary for the operation of the dispenser. Alternatively, a computer (not shown) may be connected to the dispenser to enter the necessary information and, in this case, the prescribing module 12 and the dispensing module 18 may be replaced by diskettes to be used with the computer. In the illustrated embodiment of the programmable medication dispenser, the righthand drawer 20 ("Drawer I") is arranged to contain and provide access to drugs which are to be taken on a specific time schedule, and the lefthand drawer 21 is arranged to contain and permit access to drugs which may be taken on demand or as needed.

In response to depression of a "Load" key 28 by the patient or at a prescheduled time, the dispenser displays on the screen 29 all medications scheduled for the day according to the drawer in which they are to be loaded. For each drug listed, the name, dose, number of pills to be loaded, type (pill or capsule) and color is shown. In addition, a clock 30 is provided to indicate the current time.

When the user depresses the "Load" key 28, the screen also displays the inquiry "Ready to load Drawer I? (time-scheduled drugs)" When the user has the specified drugs ready, he depresses a "Yes/Enter" key 31. As a result, the drawer 20, which has a series of twelve compartments 32 arranged in three rows, is extended. Each compartment has an indicating light 33 and the compartment to be loaded first is designated by flashing of the corresponding indicator light. At the same time, the screen 29 displays a highlighted command "Load (name of drug)" and a low-lighted and flashing "Loading" as well as a highlighted and flashing "Confirm" and a low-lighted "(name of drug) not yet confirmed". The different graphic character of each of the screen displays emphasizes the responses required from the user. After placing the proper drug in a specified compartment, the user must depress a confirm key 34 on the top of the dispenser housing. If a confirming entry has not been made, the compartment light and the load instruction on the screen 29 continue flashing and the drawer 21 cannot be closed nor can further dispensing operations proceed. If the user tries to close the drawer, an audible alarm 36 is initiated and an appropriate message is flash-displayed on the screen. The audible alarm may be a tone or ringing sound or it may consist of a vocal synthesis or recording providing specific instructions. Similarly, the instructions and information displayed on the screen 29 may be supplemented by or substituted by corresponding vocal information.

When the confirm key 34 is actuated, the flashing compartment light is turned off and the screen 29 displays "You have just loaded (name of drug)" and "Ready to load next drug?". When the user operates the "Yes/Enter" key 31, the screen indicates the next drug to be loaded with the same type of display used for the first drug, and the corresponding compartment light 33 begins flashing and, after loading of that drug in the appropriate compartment, the user again depresses the confirm key 34. This procedure continues until all of the time-scheduled drugs have been loaded into corresponding compartments in the drawer 21 in the manner indicated on the screen 29. The screen then shows "All time-scheduled drugs have been loaded and confirmed" along with a command-prompt "Close Drawer I". Thereafter, the time-scheduled drawer 21 can be closed.

When the drawer 20 is closed, the screen displays "Ready to load Drawer II?". When the Yes/Enter key 31 is depressed, the drawer 21 slides open, the indicator light 33 in the compartment for the first-listed demand drug flashes and the screen displays "Load (name of drug)" along with a flashing low-lighted "Loading" indication, a highlighted flashing prompt "Confirm (name of drug)" and a low-lighted "(name of drug) not yet confirmed". After loading the specified drug into the indicated compartment, the user presses the Confirm key 34 and the screen then reads "You have just loaded (name of drug)" and "Ready to load next drug?". When the Yes/Enter key is depressed, the screen displays the next drug to be loaded and the same procedure is repeated for loading of all of the as-needed drugs. After all of the demand drugs have been loaded and confirmed, the display shows "All Drawer II drugs loaded and confirmed" and "Close Drawer II".

After the drawer 21 has been closed, the screen 29 displays "All drugs loaded and confirmed" and "Ready to set time-scheduled drugs?". When the user enters "Yes/Enter" by depressing the key 31, the screen displays:

Time-Scheduled Drugs

The first pill to be taken?
   Upon waking?
   At specific time?
   As needed?

The user then selects one of these choices by appropriate operation of the "Select" button 38 or the "Scroll" button 39 and then keying the "Yes/Enter" button 31.

If "Upon waking" is selected by the user, the display will read: "Ready to dispense: Take first pill(s) upon awakening". The display can also sequence-in here: "Wake-up alarm?" and, if selected, the alarm time is entered by the user.

If "Specific time" is selected, the screen will display the "Time-Set" procedure. Once the time is set, it reads: "Ready to Dispense: Take first pill(s) at: (set time)".

If "As [first] needed" is selected, the display reads: "Ready to dispense: Take first pills when needed".

If appropriate, the foregoing options can be preset by the prescribing instructions in the prescribing module 12 and thus not be available as a choice. In the case of medications that need to be taken before meals, the screen 29 will display, in a "Message" or "Reminder" section of the screen, next to these last two choices, a flashing sideline: "Must be taken before first meal".

The iterative procedure allows setting and changing of mealtimes, bedtimes and special times according to the user's changing schedule.

The same procedure is followed with respect to each of the other drugs.

In operation, the dispenser's alarm 36 will go on at the scheduled time and remain on until "Dispense" key 40 is pressed, or until a preset number of minutes has passed. The alarm will be repeated a preset number of minutes later and continue to go off and on intermittently until the "Dispense" key is operated.

When the "Dispense" key 40 is then operated, the drawer 20 slides open, optionally only far enough to expose the first row of compartments, and the indicator light 33 in the appropriate compartment 32 emits a flashing light. In addition, the screen 29 displays a highlighted command-prompt: "Take (number of pills and name of drug)" and instructions for taking it along with a low-lighted and flashing "Dispensing", a highlighted flashing prompt "Confirm (name of drug)" and a low-lighted "(name of drug) not yet confirmed". The user removes the specified number of pills from the indicated compartment 32 and takes them according to the displayed instructions. When (and only when) a "Confirm" entry is made by depressing the key 34, the flashing indicator light 33 is turned off. As with all confirming entries, unless there is a proper "Confirm", no subsequent operation of the dispenser 12 can take place and any attempt to close the drawer 20 will set off the alarm 36. The display screen 29 will indicate the further action necessary to satisfy the confirm requirement. The requirement for a "confirm" entry also applies to a confirmation that instructions stated on the screen have been followed or that required reaction responses of the patient have been entered.

The screen then reads "You have just taken (name of drug)" and prompts "Ready to take next drug?". When the Yes/Enter key 31 is keyed, the screen displays the next drug to be dispensed and the same procedure will be followed until all of the drugs to be taken at that time have been taken and confirmed. If desired, a list of all those drugs, indicated "Confirmed", can then be displayed.

The screen 29 then reads "Time-group #1 is dispensed and confirmed" and prompts "Close drawer I". When the drawer 21 is closed, the screen then displays continuously the next scheduled dispensing time and a list of pills in the next group to be taken.

This procedure is repeated for each time group throughout the day as long as all scheduled drugs have been taken and confirmed.

If the appropriate confirming entry has not been made at a scheduled time, the alarm 36 continues to go on and off, the screen 29 shows a flashing "Dispensing delayed" and displays the delayed drugs, the last time taken, the time scheduled to be taken, and the number of minutes late are displayed. When the "late" user keys the Dispense key 40, the display 29 indicates which drugs dispensed from the drawer 20, if any, require a dosage adjustment, any special instructions, and prompts any "Drug response" queries, and then reschedules the remaining time groups according to the prescribing instructions recorded in the prescribing module 12. Again, a confirming entry is required in order to permit the program to continue.

For selected drugs in the scheduled-drug regimen, the user may wish to take a scheduled drug early. By operating an override key 42 and then the Dispense key 40, a list of the next drugs to be taken is displayed on the screen 29. The desired drug is selected by operating the Select key 38 and the Yes/Enter key 31 is depressed. Depending on the parameters set in the prescribing data storage module 12 by the physician, the screen may display a warning that it is too early to take that drug and that the user should wait a specified time before taking it. Alternatively, if use of the drug at that time is permissible, the screen will display a statement that the drug is being taken a specified length of time prior to the scheduled time and the user will be asked if he wants to take that drug now. If the user then depresses the Yes/Enter key 31, the drawer 20 will open and the appropriate indicator light 33 will flash. After the drug has been taken, the usual confirming entry by depression of the Confirm key 34 is required to close the drawer. The dispenser will then reset the schedule for that drug so that the prescribed interval between taking of the drug remains constant and the remaining schedule conforms to instructions.

The medication dispenser 12 accommodates as-needed drugs in the drawer 22 as described above for which there is no fixed scheduling and/or variable dosages. The prescribing instructions specify the parameters for each drug, such as minimum intervals, cumulative maximum dosage, daily, etc.

When the user needs to take a demand pill, he depresses a "Demand" key 43 and a list of all on-demand drugs appears. The specific drug is scrolled by the key 39 or selected by the key 38 and the appropriate display appears on the screen 29. Included in the display is specified information, such as last time taken, elapsed time, cumulative dosage, maximum daily dosage remaining, etc.

When the Dispense key 40 is operated, the drawer 22 opens and from then on the on-demand drug is treated like any scheduled medication.

Whether schedule-based, on-demand or confirming-entrybased, the medication dispenser can present specific prompted requests or messages for the patient's response to medication which are selected by the physician from a menu of such messages or devised by him when the prescribed instructions are set. Such messages can include prompted inquiries as to efficacy, counterindications, interactions and the like. Responses to such inquiries are required and are equivalent to confirming entries in that a nonentry is unacceptable and will prevent further operation of the dispenser. Specific response entries can be set to cause alarms and the display of responding instructions, such as an instruction to stop taking a specific drug, a delay in the next time for taking the drug, a change in the dosage or an instruction to call the physician, as well as rescheduling messages.

The programmable medication dispenser 13 of the invention can also be used for logging of symptoms or conditions of the patient. This can be scheduled at specific times during the day, at which times the alarm 36 is sounded and the screen 29 displays a menu of possible symptoms, or it can be patient-initiated in response to depression of a Log key 46. In either case, a list of possible symptoms such as nausea, headache, blurred vision, pain and the like is displayed and the user can select the appropriate symptom and enter it by depressing the Yes/Enter key 31 or, if a computer is connected to the dispenser, a description can be entered through the computer keyboard. The resulting information, requiring a confirming entry, is recorded in the prescribing module 12.

Drugs which are taken based upon events that are independent of specific times, such as at mealtimes, upon waking or retiring, after a bowel movement or the like, can be displayed continuously on the screen 29 with appropriate instructions. Such drugs are loaded in the lefthand drawer 21 and are displayed and treated like any on-demand medication. Times can be reset as events change.

The medication dispenser has a continuously running clock 30 and, if desired, a calendar (not shown). Any time a confirming entry or a response entry is executed, the entry which it confirms can be set by the prescribing instructions to be time-recorded into the medication dispenser memory and in the prescribing module memory.

The dispenser 13 can also maintain a count of the number of pills remaining within each compartment of the dispenser, as well as a running count of bottled inventory, and provide alert signals for reordering drugs for which there is less than a specified supply, such as three days. In addition, the user can at any time call up on the screen 29 any information available in the memory such as the next scheduled or previous time-group or a drug-by-drug record or schedule. Furthermore, the physician can encode in the prescribing module 12 appropriate instructions for nonprescription medication, which will then be displayed on the screen 29 prior to use of that medication.

If desired, the dispenser 13 can also be programmed to display laboratory test data, specific procedures such as bandage-dressings, topical applications, therapies, appointments and the like upon request by the user and other information relating to the patient or to other drugs, prescriptions or emergency procedures. Preferably, the alarm 36 in the dispenser is loud enough to be heard by a user in another part of the house or apartment in which the user is living. In addition, since the dispenser is readily portable and may be moved from place to place in the user's home, a handheld locator can be carried by the user to activate the alarm 36 to enable the user to identify the location of the dispenser. Conversely, the dispenser can be arranged to transmit alarm signals to the locator which is carried by the user. Such remote signalling systems are conventionally used, for example, in cordless telephone systems and are well known to those skilled in the art and therefore need not be described in detail.

In ordinary use, the data recorded by the patient's dispenser regarding usage, symptoms, answers to questions and the like is supplied to the physician by simply bringing him the patient's prescribing module 12. This data is retrieved by the physician's computer 11 to update the patient's file card diskette.

For those cases where frequent monitoring is desired, an accessory modem may be provided for direct telephonic transmission to the physician. This allows data from the patient's dispenser to go directly into the physician's computer and, conversely, the physician can transmit prescribing instructions directly to the dispenser for recording in the prescribing module 12.

Figure 4:
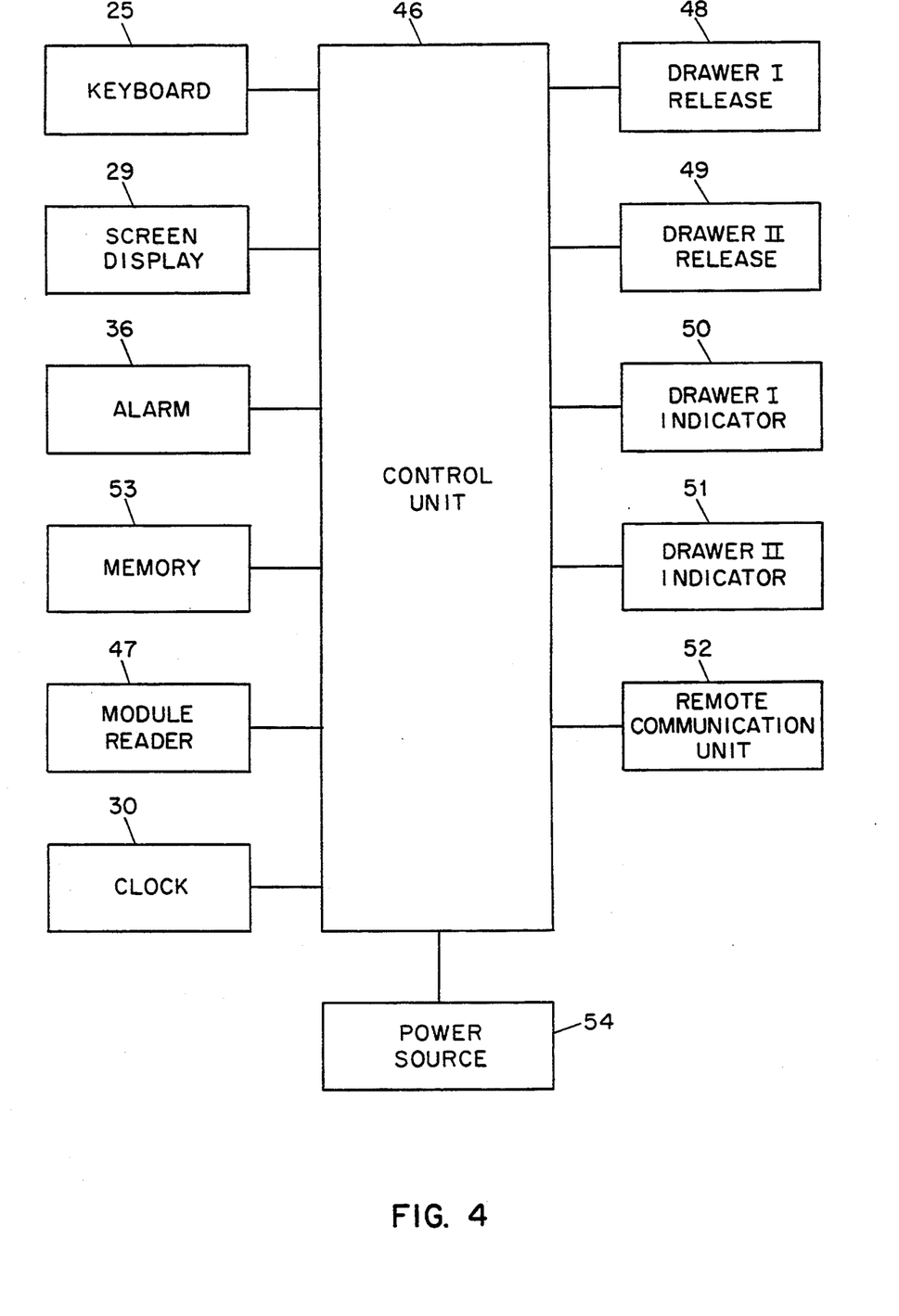
FIG. 4 is a schematic block diagram showing the major components of a typical medication dispenser in accordance with the invention.

A schematic block diagram showing the operative components of a typical dispenser is illustrated in FIG. 4. As shown there, the dispenser includes a control unit 46 containing a conventional microprocessor programmed in a conventional manner to control the above-described and other functions of the dispenser in response to information read by a module reader 47 from the prescribing module 12 and instructions entered by operation of the keys on the top of the dispenser unit. The control unit interacts with release mechanisms 48 and 49 for the drawers 20 and 21 of FIG. 3 and with indicator light control units 50 and 51, respectively, for those drawers.

In addition, the control unit 46 interacts with the keyboard 25, the screen 29, the alarm 36 and the clock 30 and with a remote communicator unit 51 which may, for example, communicate with one or more of a handheld locator, a telephone interface modem, an external printer, an infrared control unit and the like. The dispenser also includes an appropriate memory unit 52 and a power source 53 containing, for example, a battery and charging unit to permit operation during power failures, while travelling or at remote locations.

For the more competent self-administering user or where greater portability is desired, a simpler version of the dispenser 13 may be provided. This may be accomplished by preprogramming the dispenser or by appropriate entries through a personal computer or by plugging in a programming module such as a smart card containing both prescribing data and dispensing data. In this case, the prescribing module is not necessary and no separate drawer need be provided for demand-only drugs. Consequently, only one compartment is required for each type of drug. The remaining operation and display functions are the same as described above and the dispensing module supplied by the pharmacist may or may not still be necessary.

If desired, the dispenser keyboard may also be provided with a "Postpone" button which may be depressed by the patient if for any reason it is desired or necessary to postpone the taking of scheduled medication. This has the effect of resetting the alarm for the postponed medication after a predetermined delay such as five minutes and, if not taken, then every five minutes thereafter or scheduled for a later time within allowable limits and also rescheduling the taking of medications for the remainder of the day. Any delay beyond the allowable limit will cause the screen to display "Call the doctor". The "Postpone" key may also be used during loading if the medication to be loaded is not ready.

The dispenser may also provide an anticipatory alarm for "critical-to-take" medications where, for example, no postponement can be permitted.

As noted above, the dispensing module 18 is arranged for one-time use by the patient in conjunction with the medication supplied by the pharmacist. In this case, the module would be arranged in the conventional manner of a coded transit system fare card or telephone toll card, for example, to permit only a single or a selected number of loadings of medication into the dispenser, after which it would no longer be operable either for a selected drug or for all drugs and would require a new prescription and reprogramming by the pharmacist. Such limited use information storage arrangements are well known to those skilled in the art and need not be described in detail. In this way, the patient would be required to have periodic check-ups by the physician before continuing with the regimen.

Figure 5:
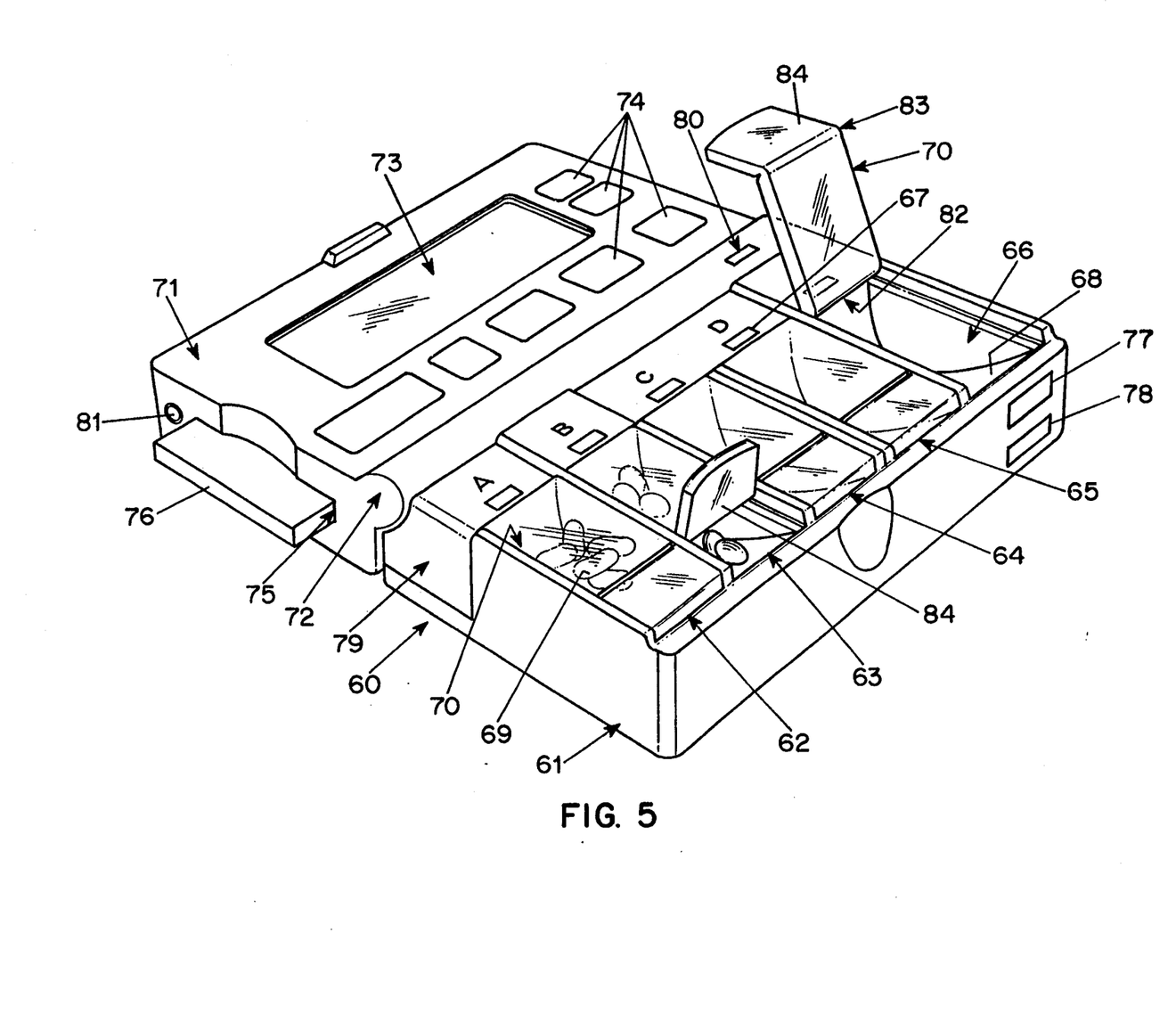
FIG. 5 is a perspective view illustrating the arrangement of another representative embodiment of a medication dispenser according to the invention.

FIG. 5 illustrates a simplified dispenser 60 designed to be conveniently portable and having dimensions, for example, of about 2 inches by 4 inches by 6 inches. In this embodiment, the dispenser includes a bottom portion 61 having five medication storage compartments 62–66, each having its own dispense indicator light 67 to indicate the compartment into which a particular medication is to be loaded or from which a particular medication is to be taken. Each of the compartments 62–66 has a bottom wall 68 which slopes upwardly toward the outer edge of the compartment to facilitate removal of pills 69 stored in the compartment and a transparent sliding or folding cover 70. The dispenser also has a top portion 71 joined to the bottom portion by a longitudinal hinge 72 to permit the parts to be folded together. The top portion 71 includes a display panel 73 and a series of buttons 74 having functions similar to those described above with respect to FIG. 3. At one end, the top portion has a slot 75 into which a single prescribing card 76 is inserted. The single card 76 may be arranged to perform the functions of both of the cards 12 and 18 described above with respect to FIG. 3. The bottom end of the dispenser has an audio alarm 77 and a visual alarm indicator 78 to permit hearing and observation of alarms when the unit is closed. The dispenser also has a battery compartment 79 containing rechargeable batteries and a low-battery indicator 80 to warn the user to recharge the batteries. The upper portion 71 also includes a port 81 for connection to a telecommunications line.

Each of the transparent covers for the compartments containing scheduled medication may normally be locked in closed position and released only for loading purposes or when medication contained in the compartment is scheduled to be used or when the patient indicates early or late taking of that medication and may also be arranged to prevent the patient from closing the cover unless the confirming entry button has been pressed.

The card 76 which is inserted into the slot 75 in the upper portion 71 of the unit may contain both physician- and pharmacist-recorded information and may also receive and store information entered by the patient.

As shown in FIG. 5, the folding cover 70 has two hinges 82 and 83 arranged to permit either the entire cover or only a front segment 84 to be pivoted away from the corresponding compartment. When only the front segment 84 is open, the user can conveniently remove a pill from the compartment by tilting or shaking the dispenser. As in the other embodiments, the double-hinged cover can be arranged to that it is released only at the time medication is to be dispensed.

Alternatively, the double-hinged cover may be openable by the user at any time and such opening is sensed by a switch engaging the front segment 84. When the switch detects opening, the screen may read "Confirm to Continue" and, after confirmation, the screen may read "Close Cover to Continue" and an alarm will be set off if an attempt is made to continue without closing the cover. Conversely, if the compartment cover is closed before a proper confirming entry is made, the display will read "Please Confirm" and further operation of the system will be prevented until the confirming entry has been made.

If the top portion 71 is folded against the bottom portion 61 while a compartment cover is still open and before a confirming entry has been made, the folding action will close the compartment cover, but further operation of the system will be prevented until the confirming entry has been made.

For a low-cost unit, the display 73 may simply be a symbol display for preformed characters and symbols whereas, for a medium- or higher-priced unit, the display 73 may be an alpha-numeric display and the keys 74 may include an alpha-numeric keypad or a separate keypad may be plugged into the unit. Higher-priced configurations may include a silicon microchip with a serial interface in the card 76 rather than magnetic storage and each such chip may have a laser-written unique electronically-readable code number for positive identification.

Moreover, the functions of several of the keys described in connection with the embodiment of FIG. 1 may be combined into a single key. For example, the Select and Scroll functions may be combined into one key and the Demand Override and Dispense functions combined into another key, and the Yes/Enter and Confirm functions may be combined into one key. Other function combinations for the same key are also possible.

Although the invention has been described herein with reference to specific embodiments, many modifications and variations therein will readily occur to those skilled in the art. Accordingly, all such variations and modifications are included within the intended scope of the invention.

I claim:

1. A medication-dispensing system comprising prescribing data storage means having a memory for storing prescription information, prescribing data entry means for encoding prescription information on the prescribing data storage means, and medication-dispensing means responsive to information stored in the prescribing data storage means including display means for displaying instructions regarding medication referred to in the information stored in the prescribing data storage means, medication container means for storing and dispensing medication, alerting means for alerting a user of a scheduled medication time in response to medication regimen information received by the dispensing means, dispense means for terminating operation of the alerting means and indicating the scheduled medication and confirming entry means requiring actuation by a user to indicate compliance with medication instructions and to terminate operation of the dispense means.

2. A medication-dispensing system comprising prescribing data storage means having a memory for storing prescription information, prescribing data entry means for encoding prescription information in the prescribing data storage means, and medication-dispensing means responsive to information stored in the prescribing data storage means including display means for displaying instructions regarding medication referred to in the information stored in the prescribing data storage means, medication container means for storing and dispensing medication in response to medication regimen information received by the dispensing means and confirming entry means requiring actuation by a user to indicate compliance with medication instructions, wherein the container means comprises a normally closed container which is released to permit access to medication and wherein the dispenser will not permit closing of the container in the absence of actuation of the confirming entry means.

3. A medication dispenser according to claim 2 including alarm means actuated in response to an attempt to close the container in the absence of actuation of the confirming entry means.

4. A medication dispenser according to claim 2 including means for preventing further operation of the dispenser in the absence of a confirming entry after the container has been released and means for recording confirming entries.

5. A medication-dispensing system according to claim 2 wherein the container is a drawer which includes a plurality of compartments for storing medication and including indicator means for indicating one of the plurality of compartments for use by a user in accordance with instructions displayed on the display means.

6. A medication-dispensing system according to claim 2 wherein the storage and dispensing means includes a second container and wherein one container contains medication to be taken on a prescribed schedule and the second container contains medication to be taken on demand.

7. A medication-dispensing system according to claim 1 wherein the medication storage and dispensing means comprises at least one container with a plurality of compartments and load means responsive to actuation by a user to display instructions regarding loading of medication into selected compartments in the storage and dispensing means.

8. A medication dispenser according to claim 1 wherein the alerting means includes alarm means for indicating the time for taking of medication and further including release means for releasing a storage and dispensing means to permit dispensing of medication in response to the alarm.

9. A medication-dispensing system according to claim 1 wherein the medication-dispensing means includes internal memory means for storing information and keyboard means permitting a user to enter information into the memory means.

10. A medication-dispensing system according to claim 1 wherein the prescribing data entry means is responsive to information contained in a medication information storage means and in a patient information storage means and includes display means for displaying medication information and patient information and keyboard means for entering and displaying prescription information and for storing prescription information on the prescribing data storage means.

11. A medication-dispensing system according to claim 1 including dispensing data storage means having a memory for storing dispensing data and dispensing data encoding means for encoding dispensing data into the dispensing data storage means and wherein the medication-dispensing means is responsive to information stored in the dispensing data storage means.

12. A medication-dispensing system according to claim 1 wherein the storage and dispensing means has a plurality of compartments for different medications and each compartment has a separate cover.

13. A medication dispenser according to claim 1 wherein the container means comprises a plurality of compartments, each having a slidable cover to permit access to medication contained therein.

14. A medication dispenser according to claim 1 wherein the container means comprises a plurality of compartments, each having a hinged cover to permit access to medication contained therein.

15. A medication dispenser according to claim 14 wherein the hinged cover has a first hinge permitting the entire cover to be opened and a second hinge permitting only an end portion of the cover to be opened to permit medication to be removed from the compartment.

16. A medication dispenser according to claim 14 including detector means for detecting the cover in the closed position.

17. A medication dispenser according to claim 14 wherein the cover is normally retained in the closed position and including release means for releasing the cover to permit access to medication in the compartment.

18. A medication dispenser according to claim 1 wherein the medication container means comprises a plurality of compartments, each having a bottom surface which slopes upwardly toward one end to facilitate removal of medication therefrom.

19. A medication dispenser comprising medication container means, data storage means removably connected to the dispenser for providing medication information to the dispenser, display means for displaying medication information including instructions regarding medication, control means responsive to the data storage means for controlling the display means to display instructions for use of medication in the medication container means, confirming entry means for actuation by a user to indicate compliance with instructions presented on the display means, and alarm means for generating an alarm signal upon closing of the medication container means prior to actuation of the confirming entry means.

20. A medication dispenser according to claim 19 wherein the removably connected data storage means comprises prescribing data storage means arranged to receive prescribing data at a remote location.

21. A medication dispenser according to claim 19 wherein the removably connected data storage means comprises dispensing data storage means arranged to receive dispensing data at a remote location.

22. A medication dispenser according to claim 19 including alarm means responsive to the control means at the selected times when medication is made accessible to the user.

23. A medication dispenser according to claim 19 including internal memory means for storing information in the dispenser and keyboard means permitting a user to enter information into the internal memory means.

24. A medication dispenser according to claim 19 wherein the medication container means includes a slidable drawer having a plurality of compartments which may be released at the selected times to permit access to one or more of the compartments and indicator means for indicating the compartment containing medication for use at the selected time.

25. A medication dispenser according to claim 19 wherein the medication container means comprises at least two drawers which are selectively releasable and wherein one of the drawers may be released at selected times in accordance with a medication regimen and another drawer is selectively releasable by the user to permit access to medication to be taken on demand.

26. A medication dispenser according to claim 19 including remote communication means permitting communication with the dispenser from a remote information source.

27. A medication dispenser according to claim 19 including remote locator means for causing the dispenser to produce a locating signal.

28. A medication dispenser according to claim 21 wherein the dispensing data storage means includes means for limiting the number of times the dispensing data stored in the storage means may be reused.

29. A medication dispenser according to claim 19 wherein the container means comprises a plurality of compartments, each having a hinged cover to permit access to medication contained therein.

30. A medication dispenser according to claim 29 wherein the hinged cover has a first hinge permitting the entire cover to be opened and a second hinge permitting only an end portion of the cover to be opened to permit medication to be removed from the compartment.

31. A medication-dispensing system comprising medication data storage means having a memory for storing medication information, display means for displaying information regarding medication stored in the medication data storage means, medication container means for storing and dispensing medication, dispense means for opening the medication container means, confirming entry means requiring actuation by a user to indicate taking of medication contained in the container means, and reminder means to remind the user to close the medication container means.

* * * * *